(12) United States Patent
Mizuma et al.

(10) Patent No.: US 9,389,282 B2
(45) Date of Patent: Jul. 12, 2016

(54) MAGNETISM DETECTION DEVICE

(71) Applicants: Independent Administrative Institution National Traffic Safety and Environment Laboratory, Tokyo (JP); HANO MANUFACTURING CO., Ltd., Fukuoka (JP)

(72) Inventors: Takeshi Mizuma, Tokyo (JP); Shinjiro Takeuchi, Fukuoka (JP)

(73) Assignees: NATIONAL AGENCY FOR AUTOMOBILE AND LAND TRANSPORT TECHNOLOGY, Tokyo (JP); HANO MANUFACTURING CO., Ltd., Fukuoka (JP)

( * ) Notice: Subject to any disclaimer, the term of this patent is extended or adjusted under 35 U.S.C. 154(b) by 0 days.

(21) Appl. No.: 14/648,862

(22) PCT Filed: Mar. 5, 2014

(86) PCT No.: PCT/JP2014/055592
§ 371 (c)(1),
(2) Date: Jun. 1, 2015

(87) PCT Pub. No.: WO2014/136825
PCT Pub. Date: Sep. 12, 2014

(65) Prior Publication Data
US 2015/0316622 A1  Nov. 5, 2015

(30) Foreign Application Priority Data

Mar. 6, 2013  (JP) .................... 2013-044383

(51) Int. Cl.
*G01R 33/04* (2006.01)
*G01N 27/60* (2006.01)
(Continued)

(52) U.S. Cl.
CPC ............... *G01R 33/04* (2013.01); *G01N 27/60* (2013.01); *G01R 33/0041* (2013.01); *G01R 33/028* (2013.01)

(58) Field of Classification Search
CPC ...... G01R 33/04; G01R 33/072; G01R 33/09; G01R 15/207; Y10T 29/49073; H05K 2201/10151
USPC ............................ 324/253, 200, 207.3, 244
See application file for complete search history.

(56) References Cited

U.S. PATENT DOCUMENTS 5,764,055 A *  6/1998  Kawase ................. G01R 33/02
                                                         324/207.13
7,420,366 B1 *  9/2008  In .......................... G01R 33/04
                                                         324/244

(Continued)

FOREIGN PATENT DOCUMENTS

JP   H07-244166 A   9/1995
JP   2004-108776 A  4/2004
(Continued)

OTHER PUBLICATIONS

International Search Report issued in PCT/JP2014/055592 mailed on Jun. 10, 2014 (2 pages).
(Continued)

*Primary Examiner* — Tung X Nguyen
*Assistant Examiner* — Giovanni Astacio-Oquendo
(74) *Attorney, Agent, or Firm* — Osha Liang LLP

(57) ABSTRACT

An apparatus for detecting magnetism includes a self-exciting fluxgate type magnetic oscillation sensor in each of three axes perpendicular to one another, the magnetic oscillation sensor including a magnetism sensor including a core-coil including a core made of a magnetic material and a coil wound around the core, and an operational amplifier circuit causing an AC excitation current to run through the coil to generate an output in accordance with a strength of an external magnetic field applied to the core. An air core coil not wound around a core is arranged in the vicinity of and in parallel with the core-coil of each of the magnetic oscillation sensors arranged in each of the axes.

3 Claims, 8 Drawing Sheets

(51) Int. Cl.
*G01R 33/00* (2006.01)
*G01R 33/028* (2006.01)

(56) References Cited

U.S. PATENT DOCUMENTS

2004/0119470 A1 6/2004 Yajima et al.
2006/0181272 A1* 8/2006 Zhang .................... G01R 33/04
324/253

FOREIGN PATENT DOCUMENTS

| JP | 2005-043254 A | 2/2005 |
| JP | 2005-069829 A | 3/2005 |
| JP | 2005-269580 A | 9/2005 |

OTHER PUBLICATIONS

Written Opinion of the International Searching Authority issued in PCT/JP2014/055592 mailed on Jun. 10, 2014 (3 pages).

* cited by examiner

MAGNETISM DETECTION DEVICE

FIELD OF THE INVENTION

The present invention relates to a magnetic oscillation sensor and an apparatus for detecting magnetism both measuring a leakage magnetic field generated by and existing in and out of a train and an automobile, and more particularly to an apparatus for detecting magnetism capable of measuring an AC magnetic field, as well as a DC magnetic field, having a frequency of about 100 kHz at maximum.

Furthermore, the present invention relates to an apparatus for detecting magnetism to be equipped in a fluxgate type magnetism detector, e.g., defined in IEC61786 standard or JIS-C1910 standard, that is, "a detector for detecting a magnetic field by virtue of non-linear magnetism characteristics of a probe or a sensor including a magnetic core made of a ferromagnetic material".

BACKGROUND ART

As a magnetic sensor for detecting a leakage magnetic field existing in and/or out of a train or an automobile, a search-coil type magnetic sensor operating by virtue of electromagnetic induction was conventionally used. However, a magnetic sensor including a coil could not detect a DC magnetic field.

A fluxgate type apparatus having been practically employed for detecting magnetism is able to detect not only a DC magnetic field, but also an AC magnetic field. However, an effective range of a frequency of a detectable AC magnetic field is merely a few kHz at maximum. A fluxgate type magnetism-detecting apparatus was not capable of detecting not only a DC magnetic field, but also an AC magnetic field having a frequency of about 100 kHz at maximum. This is because it is extremely difficult to convert a magnetic field in the range of a DC magnetic field to an AC magnetic field having a frequency of about 100 kHz and having the same magnetic field strength as that of a DC magnetic field, into electric signals having a constant strength, and further, it is also extremely difficult to guarantee the performance to do so.

In these years, there were fabricated a lot of trains from which a strong leakage magnetic field was generated, and it is afraid that a leakage magnetic field exerts harmful influence onto human beings and/or magnetic storage medium, and accordingly, "Railway rolling stock-Measuring methods of leakage magnetic field (JIS E 4018)" was defined by Japan Industry Standards Research Committee.

The method defines objects to be measured, and conditions under which measurement is to be carried out. The objects include a leakage magnetic field (magnetic flux density), and devices from which a magnetic field is generated, both existing in and out of a train. The conditions are defined in accordance with a status of a train. For instance, while a train is running, a leakage magnetic field in a train and in the vicinity of a device generating a magnetic field should be measured at a speed range of a train at which a maximum current runs through the device. Since a DC magnetic field having a magnetic flux density in the range of about 1 to about 2 mT is measured when a train starts running, a measurement device including Hall element is employed.

Specifically, X-, Y- and Z-components of a magnetic field are measured by means of a measurement device having an accuracy of about ±5%, the measured components are synthesized in accordance with the equation (1), and a magnetic flux density is expressed with the synthesized components. In recording the measurement results, a magnetic flux density is recorded in the form of both a synthesized density and components in each of axes.

$$B=(B_x^2+B_y^2+B_z^2)^{1/2} \quad (1)$$

In the measurement of a magnetic field, X-, Y- and Z-components are basically concurrently measured. Since a conventional measurement device is a generally used device displaying an effective value or a wave-height value, performances for accomplishing instantaneous measurement of a waveform, and wide band frequency characteristics are not guaranteed, and accordingly, a synthesized value in measurement of an AC magnetic field was calculated in accordance with the equation (1), based on effective values associated with X-, Y-, and Z-axes or wave height values. As a result, since a maximum value of synthesized magnetic fields is calculated with both data simultaneity and phase relation among X-, Y-, and Z-components being ignored, the thus calculated value is not consistent with a true total magnetic force (a strength or an absolute value of a magnetic field vector) to be calculated with instantaneous values of X-, Y-, and Z-axes This is because displayed effective values or wave-height values do not put data indicative of a phase relation among X-, Y-, and Z-components into consideration. For instance, a strength of a magnetic field (a strength of a magnetic field vector) calculated based on displayed wave-height values is always greater except particular cases than a true total magnetic force calculated based on data obtained when the X-, Y-, and Z-components are simultaneously measured, and has an error equal to or greater than a couple of tens %, which is remarkably beyond an allowed accuracy of ±5% of a measurement device. As a result, a synthesized value of a magnetic field calculated based on a displayed wave-height value is remarkable different from a true strength of a magnetic field vector due to an error caused by ignorance of a phase relation.

In another point of view, a conventional measurement device for measuring a magnetic field based on displayed effective values or wave-height values is of a device disregarding a distortion and/or a phase relation in waveforms of a magnetic field, and measuring an average with respect to a time as a strength of a magnetic field, and never guaranteed both instantaneous response performance to a magnetic field have high frequency components, and characteristics of accurately reproducing waveforms of a measured magnetic field.

A frequency band of a magnetic field generated from an automobile and a train broadly covers a magnetic field in the range of a DC magnetic field to an inverter frequency, and a high-frequency noise magnetic field caused by switching. In order to analyze these magnetic fields with FFT (Fast Fourier Transform), it is necessary to use a wide-band type device for measuring a magnetic field as a practical device capable of measuring, with a constant detection sensitivity, magnetic fields including not only a low-frequency band such as a DC magnetic field, a variable magnetic field, and a magnetic field for a commercial frequency, but also a high-frequency band of about 100 kHz.

Furthermore, the wide-band type device for measuring a magnetic field is required to have a remarkably wide dynamic range, specifically, to be able to measure magnetic fields ranging from a strong magnetic field of a couple of mT to a weak magnetic field in the range of hundreds of nT to tens of nT which is afraid to be exert a harmful influence to human bodies.

A system for detecting magnetism in a magnetic sensor includes, in dependence on a theory for measuring magnetism, a system suitable for measuring from a DC magnetic field to a DC variable magnetic field of a couple of Hz, a system suitable for measuring from a DC magnetic field to a DC variable magnetic field of hundreds of Hz, a system capable of measuring only an AC magnetic field in the range of a couple of Hz to tens of kHz, a system capable of measuring only a weak magnetic field, a system capable of measuring only a strong magnetic field, and so on.

For instance, a Hall element type magnetic sensor has a practically effective accuracy of about tens of µT, and accordingly is suitable for measuring a strong magnetic field, since a small magnetic field of about tens of µT may be ignored as an error when a strong magnetic field in the range of about 1 to about 2 mT is measured. However, when a weak leakage magnetic field of a couple of µT or less which is afraid to exert a harmful influence onto human bodies is measured, an error is greater than signals, and hence, signals indicative of a weak magnetic field are mixed with noises, and thus, cannot be found. Thus, the Hall element type magnetic sensor has merits and demerits.

Thus, a technique was invented in which a low frequency band and a high frequency band both including a DC magnetic field are measured by means of two types of magnetic sensors, respectively.

Specifically, the patent document 1 by the title of "An apparatus for and a method of measuring a magnetic field in railway rolling stock" discloses a complex type magnetic sensor including a combination of a magnetic oscillation sensor and a search coil type magnetic sensor, both of which complement shortcomings of each other to thereby be able to measure a wide band magnetic field. Herein, the magnetic oscillation sensor belongs to a fluxgate (IEC 61786 Definition of Standard) measuring a magnetic field by virtue of non-linear magnetic characteristics of a probe or a sensing part having a ferromagnetic core.

More specifically, the complex type magnetic sensor includes, as a first three-axis magnetic sensor, a search coil type sensor being good at detecting an AC magnetic field having a frequency of tens of Hz or greater, and, as a second three axis magnetic sensor, a magnetic oscillation sensor suitable for measuring a DC magnetic field or a variable magnetic field. By combining strong points of these two types of magnetism detection systems, the complex type magnetic sensor has no objects which cannot be measured by itself.

Each of the first and second three-axis magnetic sensors is designed to include a magnetism sensing part having a magnetism detection axis (a direction in which a magnetism sensing part senses maximum magnetism). Three magnetism detection axes are arranged to be perpendicular to one another to thereby make it possible to detect an external magnetic field by separating the external magnetic field into X-, Y-, and Z-components.

FIG. 7 illustrates a magnetic sensor disclosed in the patent document 1, having a basic construction in which each magnetism sensing part is housed in and is integral with a sensor casing.

A first three-axis magnetic sensor 51 includes a magnetism sensor for measuring only an AC magnetic field. The magnetism sensor is comprised of three search coils perpendicular to one another. Magnetic field signals (inductive voltages) detected by the search coils arranged in X-, Y-, and Z-axes are transmitted to a main measurement unit through a sensor cable 53, processed in a signal circuit, and then, output.

A second three-axis magnetic oscillation sensor 52 is comprised of a magnetic oscillation sensor for measuring a DC magnetic field and a low-frequency magnetic field. The magnetic oscillation sensor includes a magnetism sensor having three core-coils each including a magnetic core made of a ferromagnetic material. Magnetism detection axes of the core-coils are arranged along X-, Y-, and Z-axes such that they are perpendicular to one another.

FIG. 8 illustrates a basic circuit of a magnetic oscillation sensor as a device for measuring a magnetic field in three axes. In FIG. 8, 100 indicates an X-axis circuit part, 104 indicates a magnetism sensing part for an X-axis, 200 indicates a Y-axis circuit part, 204 indicates a magnetism sensing part for a Y-axis, 300 indicates a Z-axis circuit part, and 304 indicates a magnetism sensing part for a Z-axis. Since the circuits for three axes have the same structure as one another, the X-axis circuit part 100 is explained hereinbelow.

The magnetic oscillation sensor has a variation circuit of a multi-vibrator. Specifically, a variation circuit of a multi-vibrator is reconstructed to be able to oscillate, by replacing fluctuation in a voltage between capacitor terminals, that is, repetition of voltage fluctuation when oscillated, with a phenomenon of particular fluctuation in a voltage between terminals of a core-coil having non-linear characteristics when an AC current runs therethrough.

Since the oscillation in a multi-vibrator circuit is generated by virtue of non-linear excitation characteristics of a magnetic material, the oscillation circuit is called "a magnetic oscillation circuit", and a magnetic sensor to which the magnetic oscillation phenomenon is applied is called "a magnetic oscillation sensor" or "a magnetic oscillation type magnetic sensor".

An oscillation current running through the magnetic oscillation circuit passes through a core-coil 105, and accordingly, excites a core 106 alternately in a positive or negative direction to thereby magnetically saturate the core 106.

The oscillation current is therefore called also "an excitation current".

The magnetic oscillation sensor in an X-axis circuit includes a magnetism sensor 104 comprised of a core-coil 105 including a core 106 as a magnetic core, an operational amplifier 108, and resistors 107, 109 and 110 electrically connected to the operational amplifier 108. The core-coil 105 includes a terminal P20 electrically connected to a non-inverted input terminal of the operational amplifier 108, and is grounded at the other end. The reference number 111 indicates a low-pass filter having a main function of attenuating magnetic oscillation frequency components included in a magnetism detection signal. The reference number 112 indicates an amplifying circuit which controls an amplitude of a voltage in accordance with a strength of an external magnetic field detected by the magnetism sensor, and outputs the thus controlled voltage through a terminal Q10.

If only an excitation magnetic field generated by an oscillation current is applied to the core 106, an excitation duration necessary for the core 106 to be magnetically saturated in a positive direction is equal to an excitation duration for the core 106 to be magnetically saturated in a negative direction, because of symmetry about an origin with respect to magnetization characteristics (B-H curve) of a magnetic material.

In another point of view, since an origin from which the core 106 starts its action is an origin of coordinate axes of B-H curve, positive and negative excitation durations necessary for the core 106 to be magnetically saturated in positive and negative directions are equal to each other, and thus, a time difference is equal to zero. Accordingly, an integration of an output voltage having a rectangular waveform in the operational amplifier 108 is equal to zero.

However, if an external magnetic field is applied to the core 106 under the above-mentioned condition, the external magnetic field overlaps an excitation magnetic field. As a result, an action point is shifted in a degree defined by a strength of the external magnetic field from an origin of coordinate axes of B-H curve, which is an origin from which the core starts its action, and hence, a gap is caused in timing at which the core is positively or negatively magnetically saturated. Specifically, a ratio between a positive half-cycle duration and a negative half-cycle duration (called "a duty ratio") in the core is varied due to the external magnetic field, and thus, an integration of an output voltage from the operational amplifier 108 also varies accordingly In other words, the external magnetic field is detected by a magnetic oscillation sensor as a fluctuation in an integration of an output voltage from the operational amplifier 108

An oscillation frequency of a magnetic oscillation sensor is initially adjusted by varying a partial voltage ratio between the resistors 109 and 110 both electrically connected to an output terminal of the operational amplifier 108 (adjustment at shipment).

However, such circuit structure as mentioned above is not ideal for the following reasons.

The first reason is that if a difference is caused in oscillation frequencies of a plurality of magnetic oscillation sensors, a signal is generated having a beat frequency (a "beat" frequency generated when two waves having frequencies slightly different from each other overlap).

In other words, a signal having a beat frequency component and not existing in an external magnetic field overlaps a detection signal as noises. It is difficult to identify a beat frequency component from a magnetism detection signal transmitted from a magnetic oscillation sensor, as a magnetic field having a beat frequency component cannot help from being recognized as an external magnetic field. Furthermore, if such phenomenon occurs, an output transmitted from a magnetic oscillation sensor will contain a fluctuation error even in a DC level in the range of about tens of nT to about thousands of nT in dependence on a strength of a disturbance magnetic field, resulting in that an environmental magnetic field cannot be accurately measured or a magnetic field cannot be measured in a strong field.

A magnetic oscillation sensor under conditions of being in a strong magnetic field has a tendency that a magnetic oscillation frequency lowers while a magnetic field is being measured, and hence, beat phenomenon readily occurs due to the fluctuation of the frequency, which is a serious defect which cancels various merits of a magnetic oscillation sensor with respect to its performances.

The second reason is that an accuracy with which a disturbance magnetic field is measured is degraded due to electromagnetic noises generated among core-coils in a three-axis magnetic oscillation sensor or electromagnetic noises generated in a neighboring search coil type magnetic sensor.

Thus, it was necessary to separate magnetism sensing parts and circuit parts in the three axes from one another, or space magnetism sensing parts in magnetic sensors from one another, when they are arranged in a sensor case. Specifically, magnetic oscillation sensors are randomly positioned with a sufficient space being among them, core-coils or search coils are randomly positioned with a sufficient space being among them, and/or a sensor case in which the sensors are housed is designed to be big enough to house magnetic sensors therein.

However, since a magnetic field is measured at each of positions of sensors in the above-mentioned solution, points at which a magnetic field is measured randomly exist, causing deterioration in accuracy of magnetic field measurements, and likelihood of measurement error is increased.

There is no problem in measurement of a magnetic field regardless of random positions of magnetic sensors, if a magnetic field is a uniform parallel magnetic field. However, in measurement of a magnetic field locally distorted with a steep disturbance of the strength of the magnetic field in or out of a train or an automobile, intensities of magnetism may be quite different from one another in dependence on random positions of magnetic sensors, resulting in measurement errors unavoidably caused due to positional gaps of magnetism sensing parts of magnetic sensors, and hence, measured intensities of magnetic fields are not reliable.

PRIOR ART REFERENCES

Patent Documents

Patent Document 1: Japanese Patent Application Publication No. 2005-69829

A fluxgate type magnetic sensor measuring a magnetic field by virtue of non-linear magnetic characteristics of a magnetic core made of a ferromagnetic material is grouped into a magnetized system and a self-exciting system in view of a process of supplying an excitation current to a core-coil equipped in a magnetism sensing part.

The former-mentioned magnetized system is of an externally exciting system in which an excitation current is supplied from an external oscillation circuit or an external AC power source both being independently separate from a core-coil. This system is published in 1939, and is presently broadly used as a basic excitation system in a fluxgate type magnetic sensor. Since a fluxgate type magnetic sensor including the system is able to effectively measure not only a DC magnetic field, but also an AC magnetic field having a frequency of a couple of kHz, the fluxgate type magnetic sensor is broadly used for measuring a weak magnetic field in a low frequency band.

The externally exciting system has to receive an excitation current from an external power source. When an external strong field having a strength of thousands of μT or greater is to be measured, an excitation current having a strength a couple of times greater than thousands of μT has to be supplied to a magnetic sensor as an AC current having a uniform strength, and furthermore, a power of excitation current to excite a core of a magnetic sensor has to be increased.

In contrast, when a weak magnetic field is to be measured, an excitation current to magnetically saturate a core may be small. However, in order to measure both a strong field having a strength of thousands of μT, and a weak magnetic field, a magnetic sensor has to be kept over-exciting for measuring a strong field as a maximum magnetic field. To this end, it is necessary to supply in vain an excitation current having a strength a couple of times greater than thousands of μT to a magnetism sensing part.

Thus, difficulties exist such as reconstruction of a magnetism sensing part, countermeasure to abnormally heated coil, and countermeasure for stabilizing an excitation current, none of which are issues in measurement of a weak magnetic field.

There is no commercially available magnetic sensor satisfying these performances demands.

SUMMARY OF THE INVENTION

In contrast, the latter-mentioned self-exciting fluxgate type magnetic sensor is called a magnetic oscillation sensor. A simplest circuit for a magnetic oscillation sensor is comprised of a variable multi-vibrator reconstructed by replacing oscillation generated by fluctuation in a voltage at a capacitor terminal in an oscillation circuit of a non-stable multi-vibrator comprised of an operational amplifier, with fluctuation in a voltage varying by virtue of non-linear magnetic characteristics of a core-coil.

Since a core-coil itself acts as a part of an oscillation circuit in the above-mentioned magnetic sensor, an oscillation current running through the oscillation circuit naturally runs through the core-coil as an excitation current. In this system, since an oscillation current running through the oscillation circuit acts as an excitation current to thereby magnetize a core-coil, it is no longer necessary to use an external AC power source for excitation. It can be said that the system is an independent self-exciting system.

In a magnetic oscillation sensor, an AC component as an excitation current component for magnetic oscillation, and a component being proportional with a strength of a disturbance magnetic field run through a core-coil. Since an integration of an excitation current running through a core-coil of a magnetic oscillation sensor is in proportion with a strength of an external magnetic field, a magnetic oscillation sensor wastes no excitation current, and can save energy with a high efficiency, unlike an excitation system such as an exciting fluxgate type magnetic sensor in which a magnetizing magnetic field having a strength greater than measurement limit has to be always generated.

A magnetism detecting apparatus according to one or more embodiments of the present invention is capable of accomplishing the above-mentioned performances of a magnetic oscillation sensor at maximum in order to make it possible to measure a magnetic field including not only a DC magnetic field, but also an AC magnetic field, in accordance with International Standard IEC/TS62597 (international standard about measurement of a leakage magnetic field in and out of a train).

For example, one or more embodiments of the present invention minimize a positional gap at a point at which a magnetic field is measured.

As another example, one or more embodiments of the present invention establish technique for preventing occurrence of beat phenomenon generated due to a difference in oscillation frequencies among magnetic oscillation sensors.

In a first aspect of the present invention, a magnetic oscillation sensor includes a magnetism sensor of a core-coil including a core made of a magnetic material and a coil wound around the core, and an operational amplifier circuit causing an AC excitation current to run through the coil to generate an output in accordance with a strength of a magnetic field applied to the core, characterized by an air core coil wherein the air core coil is positioned in the vicinity of the core-coil of the magnetism sensor, and a current by which a magnetic field having the same strength as that of a leakage magnetic field generated due to an excitation current running through the core-coil, and further having a direction opposite to a direction of the leakage magnetic field is supplied to the air core coil.

In one or more embodiments, it is important to minimize a positional gap at a point at which a magnetic field is measured, in order to enhance an accuracy with which a magnetic field is measured. In order to enhance the accuracy, it is necessary to position core-coil sensors of magnetism sensors close to one another to house them in a small-sized sensor case. To this end, it is necessary to possibly avoid electromagnetic induction among core-coils of magnetism sensors to thereby possibly suppress induction noises.

In the first aspect of the present invention, a system is adopted in which, in order to reduce influence to be exerted onto core-coils of adjacent axes to thereby possibly suppress induction noises, an excitation current is supplied not only to a core-coil of a magnetism sensor measuring a magnetic field, but also to an air core coil to thereby cause the air core coil to generate a magnetic field having the same strength as that of a leakage magnetic field, and further having a direction opposite to a direction of the leakage magnetic field for canceling the leakage magnetic field.

Since this system make it possible to minimize a space into which a leakage magnetic field leaks out of a magnetism sensor, the system is useful when a magnetic field is measured only by means of a magnetic oscillation sensor, ensuring that induction noises to be generated in adjacent electronic devices and circuits can be possible suppressed.

In a second aspect of the present invention, a magnetism detecting device includes a plurality of magnetic oscillation sensors each comprised of a magnetism sensor having a core-coil including a core made of a magnetic material and a coil wound around the core, and a multi-vibrator including the coil of the core-coil, a circuit element, and an operational amplifier circuit, characterized in that an oscillation synchronization signal circuit network is reconstructed in which the operational amplifier circuits in the magnetic oscillation sensors are electrically connected to one another through electric connectors to thereby unify an oscillation frequency of the magnetic oscillation sensors, and each of the cores of the magnetism sensors are compulsorily excited by a unified magnetic oscillation frequency by virtue of a synthesized excitation current including an oscillation synchronization signal running through the oscillation synchronization signal circuit network, and an excitation current output from the operational amplifier circuit.

In the second aspect of the present invention, a circuit is constructed to share magnetic oscillation frequency components of a plurality of the magnetic oscillation sensors. In order for each of the cores to be excited by a common magnetic oscillation frequency unified by the shared data of the circuit, the operational amplifier circuit are electrically connected to one another to thereby construct an oscillation synchronization signal circuit network. Beat phenomenon is prevented by an oscillation synchronization signal running through the circuit network.

In a third aspect of the present invention, output terminals of the operational amplifier circuits in the magnetic oscillation sensors are connected in a loop through passive or active elements in the oscillation synchronization signal circuit network mentioned in the second aspect of the present invention.

In the third aspect of the present invention, the output terminals of the operational amplifier circuits are connected through passive or active elements to thereby define a loop-type oscillation synchronization signal circuit network. Each of the cores of the magnetism sensors are compulsorily excited by a unified magnetic oscillation frequency by virtue of a synthesized excitation current including an oscillation synchronization signal running through the oscillation synchronization signal circuit network, and an excitation current output from the operational amplifier circuit.

In a fourth aspect of the present invention, output terminals of the operational amplifier circuits in the magnetic oscillation sensors are connected in a star through passive or active elements in the oscillation synchronization signal circuit network mentioned in the second aspect of the present invention.

In the fourth aspect of the present invention, the output terminals of the operational amplifier circuits are connected through passive or active elements to thereby define a star-type oscillation synchronization signal circuit network. Each of the cores of the magnetism sensors are compulsorily excited by a unified magnetic oscillation frequency by virtue of a synthesized excitation current including an oscillation synchronization signal running through the oscillation synchronization signal circuit network, and an excitation current output from the operational amplifier circuit.

In a fifth aspect of the present invention, the second aspect of the present invention is modified so an external signal transmitting circuit transmitting an electric signal having the same frequency as that of the above-mentioned unified magnetic oscillation frequency is electrically connected to the operational amplifier circuit through an electrical connector to thereby construct an oscillation synchronization signal circuit network having a fixed unified magnetic oscillation frequency.

In the fifth aspect of the present invention, an external signal transmitting circuit transmitting an electric signal having the same frequency as that of the above-mentioned unified magnetic oscillation frequency is electrically connected to the operational amplifier circuit through an electrical connector to thereby construct an oscillation synchronization signal circuit network having a unified magnetic oscillation frequency. Each of the cores of the magnetism sensors are compulsorily excited by a unified magnetic oscillation frequency by virtue of a synthesized excitation current including an oscillation synchronization signal running through the oscillation synchronization signal circuit network, and an excitation current output from the operational amplifier circuit.

In a sixth aspect of the present invention, each of the second to fifth aspects of the present invention is modified so each of the magnetic oscillation sensors is designed to include an air core coil mentioned in the first aspect.

By applying the magnetic oscillation sensor including the air core coil to each of the second to fifth aspects of the present invention, it is possible to prevent a leakage magnetic field leaking from a core-coil of each of the magnetic oscillation sensors from exerting a harmful influence onto detection carried out by the other magnetic oscillation sensors, ensuring enhancement in an accuracy with which a magnetic field is measured.

One or more embodiments of the present invention provide one or more of the following advantages. One or more embodiments of the present invention relate to the improvement applied to a conventional magnetic oscillation sensor under International Standard IEC/TS62597. One advantage of the present invention is that an applied magnetic field can be canceled by a current running through a core-coil as long as normal oscillation condition is maintained, and hence, it is possible to measure a magnetic field having a strength of thousands of μT or greater, and a magnetic field ranging from a DC magnetic field to an AC magnetic field having a frequency of about 100 kHz.

A lower limit of a strength of a magnetic field to be measured lowers to a couple of nT by virtue of reduction in noise level, and a dynamic range of a strength of a magnetic field to be measured is in the range of a strong field having a strength of a couple of mT to a weak magnetic field having a strength of a couple of nT or smaller. It is possible to measure a magnetic field in a wide range.

Furthermore, it is possible to measure a magnetic field in a wide range frequency covering from a DC magnetic field to an AC magnetic field having a frequency of about hundreds of kHz by means of a single magnetism detection system, specifically, a magnetic oscillation sensing system without applying a plurality of magnetism detecting systems to measurement ranges, respectively. This performance is about twenty times greater than the same of a conventional fluxgate type magnetic sensor having a maximum frequency of about 5 kHz.

Since a magnetic oscillation sensor is of an energy-saving type magnetic sensor in which an excitation current for magnetizing a core is in proportion with a strength of an external magnetic field, it is suitable for simultaneously measuring a strength distribution of a variable magnetic field at a plurality of measurement points.

As mentioned above, the magnetism detection device in accordance with one or more embodiments of the present invention provides sufficient performances as a magnetic sensor for measuring a magnetic field in a train or an automobile. In addition, the magnetism detection device in accordance with one or more embodiments of the present invention is expected to be broadly employed as one of useful high-performance magnetic sensors in study and research in other technical fields, in industrial fields, and/or in measurement of a magnetic field generated from a power-feed line or an environmental magnetic field.

BRIEF DESCRIPTION OF THE DRAWINGS

FIG. 1 illustrates surroundings of a magnetism sensing part of a magnetic oscillation sensor in accordance with an embodiment of the present invention.

FIG. 2 illustrates surroundings of a magnetism sensing part of a conventional magnetic oscillation sensor.

DETAILED DESCRIPTION OF EMBODIMENTS

Embodiments in accordance with the present invention will be explained in detail hereinbelow with reference to drawings.

FIG. 1 illustrates surroundings of a magnetism sensing part of a magnetic oscillation sensor in accordance with an embodiment of the present invention, and FIG. 2 illustrates surroundings of a magnetism sensing part of a conventional magnetic oscillation sensor.

Figure 2A:
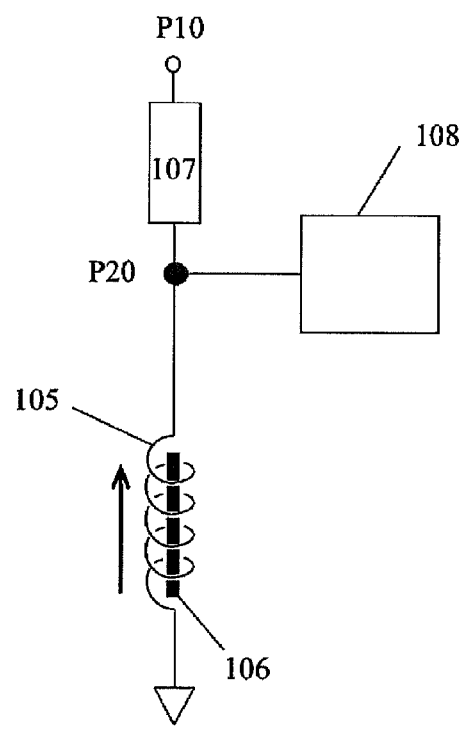
FIG. 2(a) is a circuit diagram.
Figure 2B:
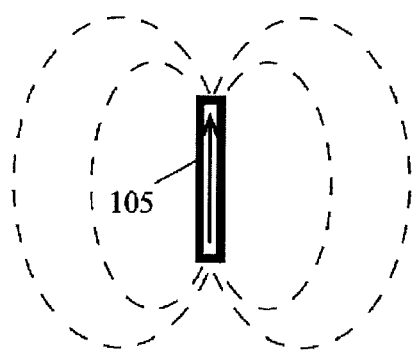
FIG. 2(b) is used for explaining a leakage magnetic field.
Figure 8:
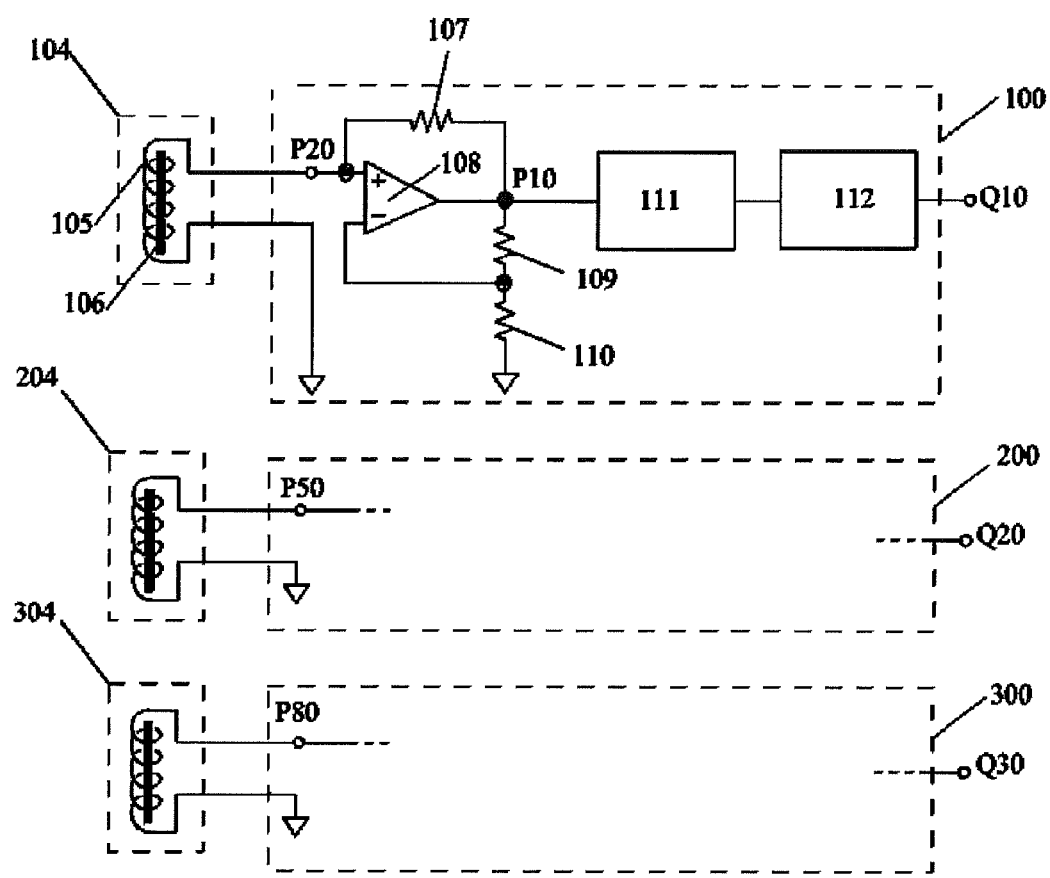
FIG. 8 is a circuit diagram of a three-axis device for measuring a magnetic field.

As illustrated in FIG. 2(a) or FIG. 8, in a conventional magnetic oscillation sensor, an excitation current is supplied to a core-coil 105 arranged around a core 106 of a magnetism sensing part via a passive element 107 such as a resistance from a terminal P10, and then, fluctuation in a voltage at a terminal P20 is detected by means of an operational amplifier 108 to thereby detect a strength of an external magnetic field. In the magnetic oscillation sensor, when an excitation current runs through the core-coil 105, a leakage magnetic field is generated around the core-coil, as illustrated in FIG. 2(a). An arrow illustrated in FIG. 2(b) shows a direction of a polarity of a magnetic field generated in the core-coil 105.

In the case that only the core-coil 105 is used, an excitation magnetic field leaking from the core-coil 105 spreads around the coil. Accordingly, an electronic device, a communication device, and electronic circuits existing in the space are naturally influenced by induction noises.

In order to protect them from induction noises, it is necessary to move them away from the magnetism sensing part, or to reduce a size of a space in which induction noises exist.

The former solution cannot be adopted in a magnetic field measurement device, because an accuracy with which measurement is carried out is deteriorated.

As the latter solution in which a size of a noise space is reduced, a magnetic shield surrounds a magnetic material. However, if a magnetic shield is located in the vicinity of a magnetism sensing part, it will be impossible to accurately measure an external magnetic field, because the external magnetic field is influenced by the magnetic shield. In the end, a sole solution for shielding a leakage magnetic field is to apply a magnetic field identical with an excitation magnetic field, in an opposite direction to thereby cancel the leakage magnetic field.

Figure 1A:
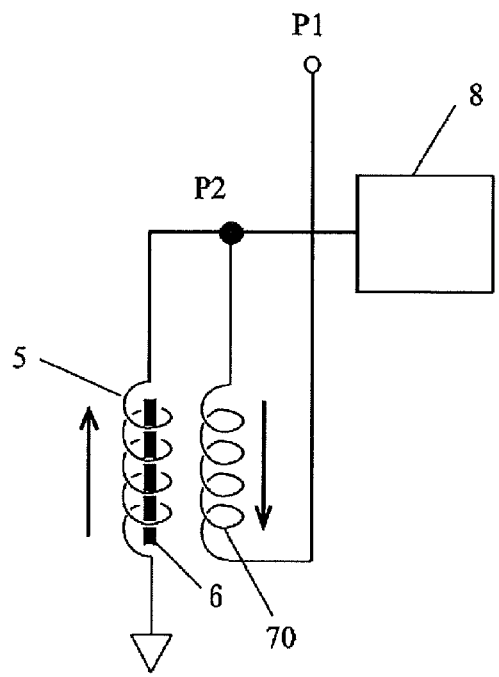
FIG. 1(a) is a circuit diagram.
Figure 1B:
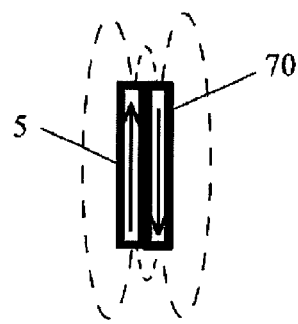
FIG. 1(b) is used for explaining a leakage magnetic field.

Thus, a magnetic oscillation sensor in accordance with the embodiment of the present invention is designed to use an air core coil 70 in place of the passive element 107 illustrated in FIG. 2, as illustrated in FIG. 1(a). The air core coil 70 is positioned possibly close to a core-coil 5 to thereby generate an inverse magnetic field. FIG. 1(b) illustrates a concept of canceling a leakage magnetic field by means of the air core coil 70. It is understood in FIG. 1(b) that a size of a noise space in which electronic devices are influenced by induction noises is reduced. Arrows illustrated in FIG. 1 show directions of polarities of magnetic fields generated in the core-coil 5 and the air core coil 70.

Figure 3:
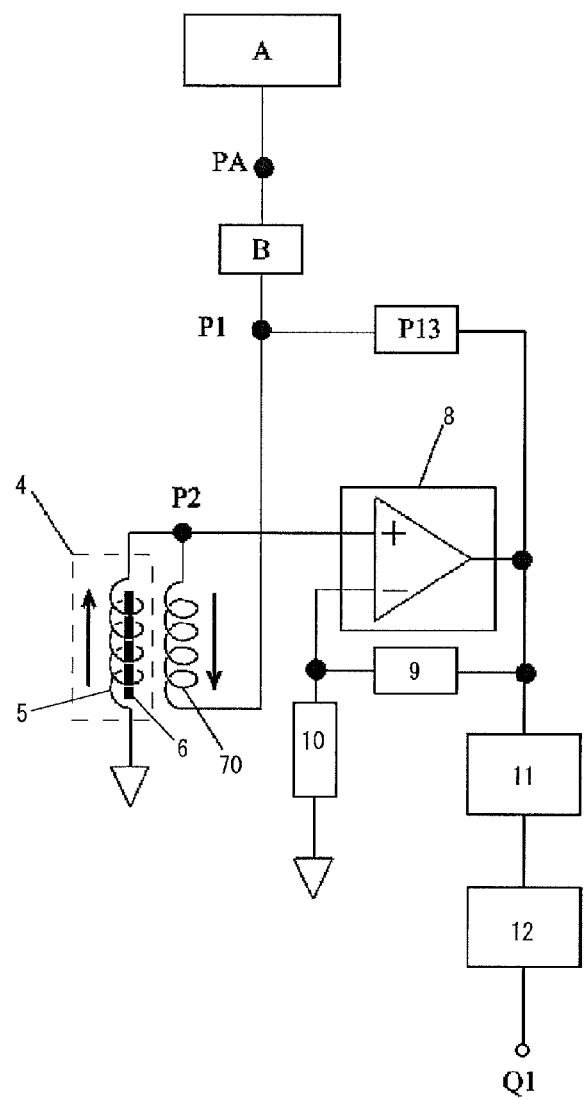
FIG. 3 is a circuit diagram of surroundings of a magnetism sensing part of a magnetic oscillation sensor in accordance with an embodiment of the present invention.

FIG. 3 illustrates an embodiment of a circuit of a single magnetic oscillation sensor capable of preventing fluctuation in an oscillation frequency which is likely to be generated when an external oscillation synchronization signal is applied to an external strong field. The illustrated circuit is a basic circuit of an external synchronization type magnetic oscillation sensor in a plurality of magnetic oscillation sensors.

"A" indicates a circuit for transmitting an external signal. This circuit is newly added externally to a magnetic oscillation sensor circuit. The external signal transmitting circuit A is designed to have a frequency by which a magnetic oscillation sensor makes oscillation most stably. A component of the frequency is transmitted as an oscillation synchronization signal to the magnetism sensing part through a terminal P1 from an output terminal PA.

A core 6 arranged in the core-coil 5 in the magnetism sensing part 4 is excited by a stable excitation current in synchronization with an oscillation synchronization signal, by means of a synthesized excitation current including the oscillation synchronization signal, and an excitation current transmitted from an operational amplifier circuit.

A connector B is comprised of an electrically passive or active element.

P13 indicates a passive element comprised of a resistance or a coil, and is designed to have such an optimal impedance that magnetic oscillation stably continues even in the case that the circuit is short-circuited.

In accordance with the embodiment, it is possible to possibly reduce a size of a space in which a leakage magnetic field leaking out from a magnetism sensing part 4 exists, by positioning an air core coil 70 in the vicinity of the core-coil 5. Thus, the embodiment is effective in measuring a magnetic field by means solely of a magnetic oscillation sensor, ensuring it possible to possibly to prevent induction noises from influencing neighboring electronic devices or circuits.

Figure 4:
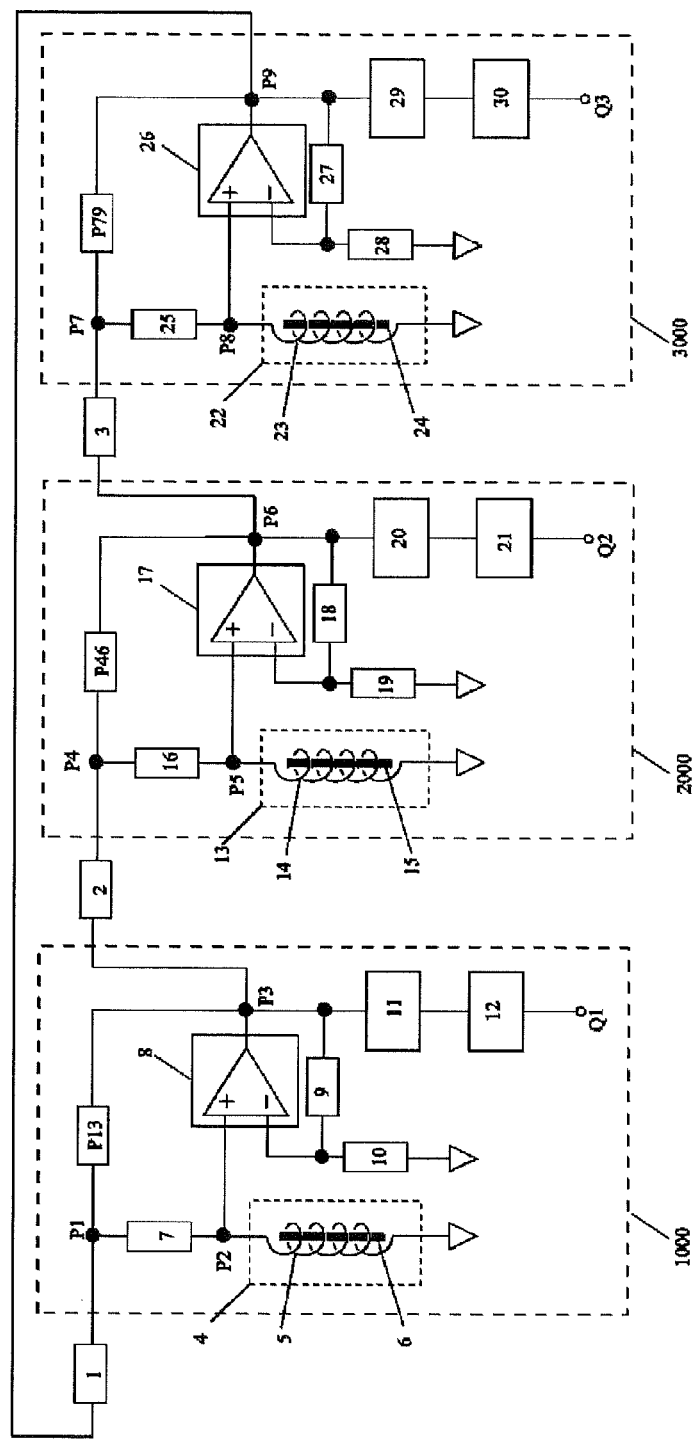
FIG. 4 is a circuit diagram of a magnetism detection device in accordance with the first embodiment of the present invention.

FIG. 4 is a circuit diagram of a three-axis device for measuring a magnetic field, in accordance with the first embodiment of the present invention. The illustrated device is comprised of three magnetic oscillation sensors as a typical example of a device comprised of a plurality of magnetic oscillation sensors.

Simultaneous measurement at multi-points where a single magnetic oscillation sensor is positioned at a plurality of measurement points, as another example of a circuit comprised of a plurality of magnetic oscillation sensors, can be explained as variation of the device mentioned hereinbelow, and hence, is not explained for avoiding complexity.

In the case that an external magnetic field is measured by means of a magnetic sensor having each sensitive axis, a process is generally used of separating a total magnetic force thereof into X-, Y-, and Z-components in vector, and individually measuring each of orthogonal components.

The three-axis device for measuring a magnetic field has a circuit comprised of a combination of a X-axis circuit part 1000, a Y-axis circuit part 2000, and a Z-axis circuit part 3000, each of which is separate from one another.

A magnetic oscillation sensor has a direction. An axial direction in which a magnetic oscillation sensor is most sensitive to a magnetic field is called a magnetic field detection axis. As an example, a magnetism sensing part including a straightly linear core, and a core-coil 5, 14 or 23 wound around the core in a direction perpendicular to a longitudinal axis of the core has a magnetic field detection axis extending in parallel with a longitudinal axis of the core 6, 15 or 24.

In the three-axis device for measuring a magnetic field in accordance with the embodiment, magnetism sensing parts 4, 13 and 22 of the magnetic oscillation sensor is housed in a sensor case such that magnetic field detection axes thereof are perpendicular from one another by slightly adjusting angles of the cores 6, 15 and 24 in axial directions thereof.

In order to measure a magnetic field with high accuracy, beat phenomenon has to be prevented from occurring. To this end, it is necessary to unify magnetic oscillation frequencies of the magnetic oscillation sensors, and magnetize the cores 6, 15 and 24 of the magnetism sensing parts with an excitation current having the thus unified frequency.

One important technique in one or more embodiments of the present invention is that the operational amplifier circuits in a plurality of the magnetic oscillation sensors are electrically connected through electrical connectors to thereby construct an oscillation synchronization signal circuit network as means for unifying frequencies in order to avoid beat phenomenon, and the cores 6, 15 and 24 of the magnetism sensing parts are excited by an excitation current having a unified frequency by virtue of a synthesized excitation current comprised of a combination of an oscillation synchronization signal running through the oscillation synchronization signal circuit network and an excitation current output from the operational amplifier circuit.

Specifically, output terminals P3, P6 and P9 of the operational amplifying circuits 8, 17 and 26 are electrically connected to output terminals P1, P4 and P7 through passive elements P13, P46 and P79, respectively. The terminals P1 and P9 are electrically connected to each other through an electric connector 1, the terminals P3 and P4 are electrically connected to each other through an electric connector 2, and the terminals P6 and P7 are electrically connected to each other through an electric connector 3 to thereby construct a loop-type oscillation synchronization signal circuit network such that they can share a signal having a unified magnetic oscillation frequency. Thus, the cores 6, 15 and 24 of the magnetism sensing parts can be excited by virtue of a synthesized excitation current comprised of a combination of an excitation current output from the operational amplifier circuit and the oscillation synchronization signal having a unified magnetic oscillation frequency.

Each of the electric connectors 1, 2 and 3 is comprised of an electric passive or active element.

For instance, a passive element having a simplest structure is a connector comprised of a single electric resistor (hereinbelow, called as "a resistor"). As an alternative, a passive element may be comprised of a resistance, a capacitor and/or a coil and so on. An electric connector may be comprised of a circuit to which a function of amplifying power is added.

In the case that each of elements indicated by the reference numbers 7, 16 and 25, and P13, P46 and P79 is to be comprised of a passive element, a resistance or a coil may be used. An impedance thereof may be 0 ohm in a case of short-circuit, that is, a case in which it is not necessary to use a passive element, in dependence on a circuit constant or a construction of an oscillation circuit.

Thus, the term "an output terminal of an operational amplifier circuit" in the specification includes not only the terminals P3, P6 and P9, but also the output terminals P1, P4 and P7, regardless of impedances of the passive elements P13, P46 and P79.

Each of the operational amplifier circuits 8, 17 and 26 is comprised of an amplifying circuit including an operational amplifier as a main component, and may be designed to additionally have a function of amplifying electric power, if necessary.

Output voltages at the output terminals P3, P6 and P9 of the operational amplifier circuits 8, 17 and 26 are divided by resistors 9 and 10, resistors 18 and 19, and resistors 27 and 28, respectively. Terminal voltages of the resistors 10, 19 and 28 are input into inversion terminals of the operational amplifier circuits. Since a magnetic oscillation frequency is defined by a voltage division ratio between the resistors 9 and 10, a voltage division ratio between the resistors 18 and 19, and a voltage division ratio between the resistors 27 and 28, a voltage division ratio is designed to be able to be slightly changed by means of a trimmer having a variable resistance.

Each of the reference numerals 11, 20 and 29 indicates a filter circuit having a function of preventing unnecessary frequency components not to be measured and/or unnecessary magnetic oscillation frequency components from being included in output voltage through output terminals Q1, Q2 and Q3.

Each of the reference numerals 12, 21 and 30 indicates an amplifying circuit for controlling amplification for the purpose of calibration. In order for a measured strength of a magnetic field to be reliable, it is necessary for the measured strength to be consistent with a strength satisfying national standards. In the calibration, a standard magnetic field generator is used having traceability relative to the national standards. A magnetism sensing part is positioned in a magnetic field generated by the standard magnetic field generator to thereby control the amplification of the amplifying circuits 12, 21 and 30.

The first embodiment is characterized in that even if fluctuation in an oscillation frequency is generated due to fluctuation in a temperature of a circuit part in a three-axis magnetic sensing device and/or external disturbance magnetic field applied to a magnetic oscillation sensor, beat phenomenon does not occur, because all of oscillation frequencies of the magnetic oscillation sensors are changed together.

Figure 5:
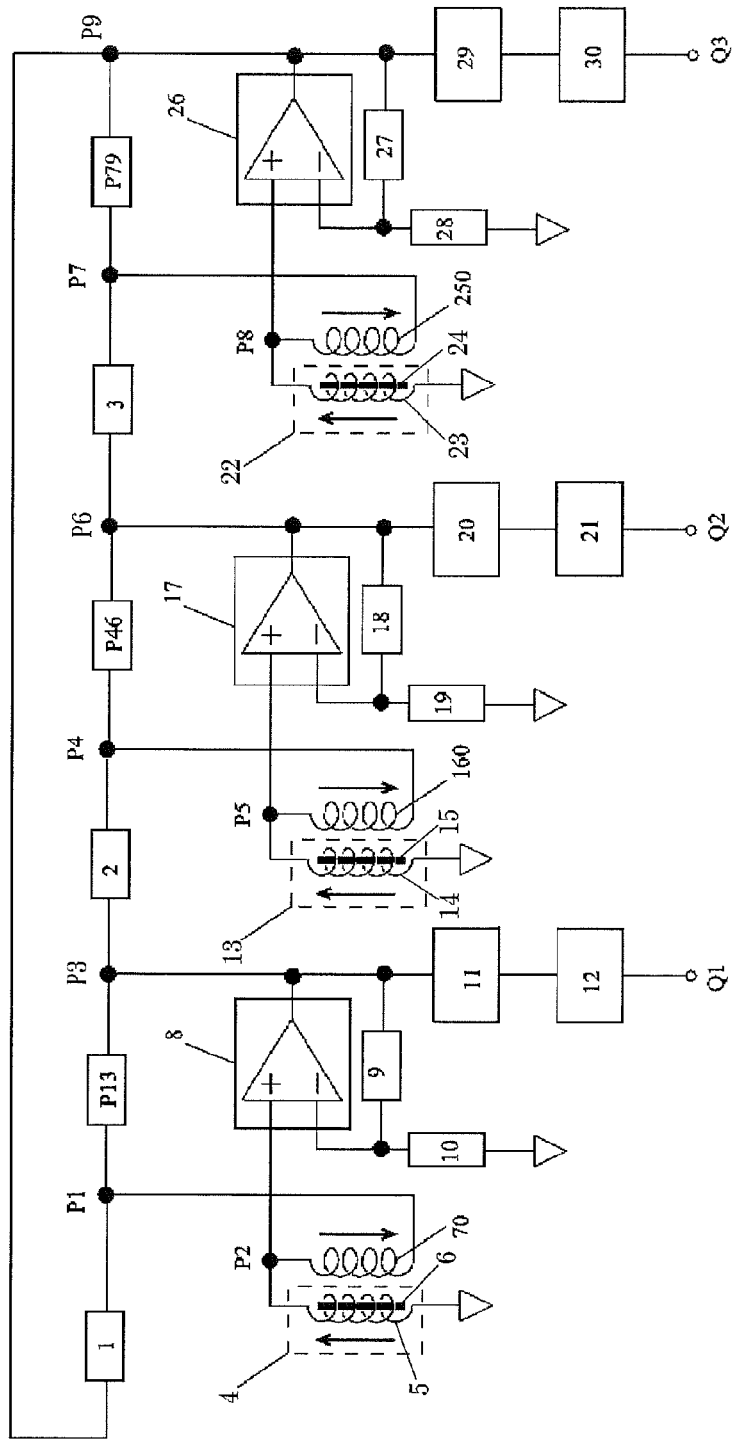
FIG. 5 is a circuit diagram of a magnetism detection device in accordance with the second embodiment of the present invention.

FIG. 5 illustrates the second embodiment in accordance with the present invention. Specifically, FIG. 5 illustrates an example of a circuit for a three-axis magnetic sensing device having a countermeasure to a leakage magnetic field. The circuit includes air core coils in order to cancel a leakage magnetic field leaking out of and radiating from a core-coil of a magnetism sensing part. The circuit cancels a leakage magnetic field radiated from a core-coil to thereby prevent harmful influences caused by electromagnetic noises from exerting on neighboring devices. The countermeasure for suppressing electromagnetic noises to neighboring devices is useful even in a single magnetic oscillation sensor.

The circuit is defined by replacing the resistors 7, 16 and 25 in the first embodiment illustrated in FIG. 4 with the air core coils 70, 160 and 250 in the second embodiment illustrated in FIG. 5 to thereby cancel a leakage magnetic field radiated from the core-coils 5, 14 and 23, respectively.

The air core coils 70, 160 and 250 are positioned in the close vicinity of the core-coils 5, 14 and 23 of the magnetism sensing parts, respectively, such that their axes in which a magnetic field is measured are in parallel with one another.

The air core coils 70, 160 and 250, and connection terminals P2, P5 and P8 through which the air core coils are electrically connected to the magnetism sensing parts are electrically connected to non-inversion terminals of the operational amplifier circuit 8, 17 and 26, respectively, to thereby define a circuit for a magnetic oscillation sensor.

Each of the cores 6, 15 and 24 in the core-coils 5, 14 and 23 of the magnetism sensing parts 4, 13 and 22, respectively, acts as a magnetic oscillation sensor to be excited by an excitation current having a unified magnetic oscillation frequency, by virtue of a synthesized excitation current comprised of an oscillation synchronization current running through an oscillation synchronization signal circuit network, similarly to FIG. 4, and an excitation current output from an operational amplifier circuit.

Figure 6:
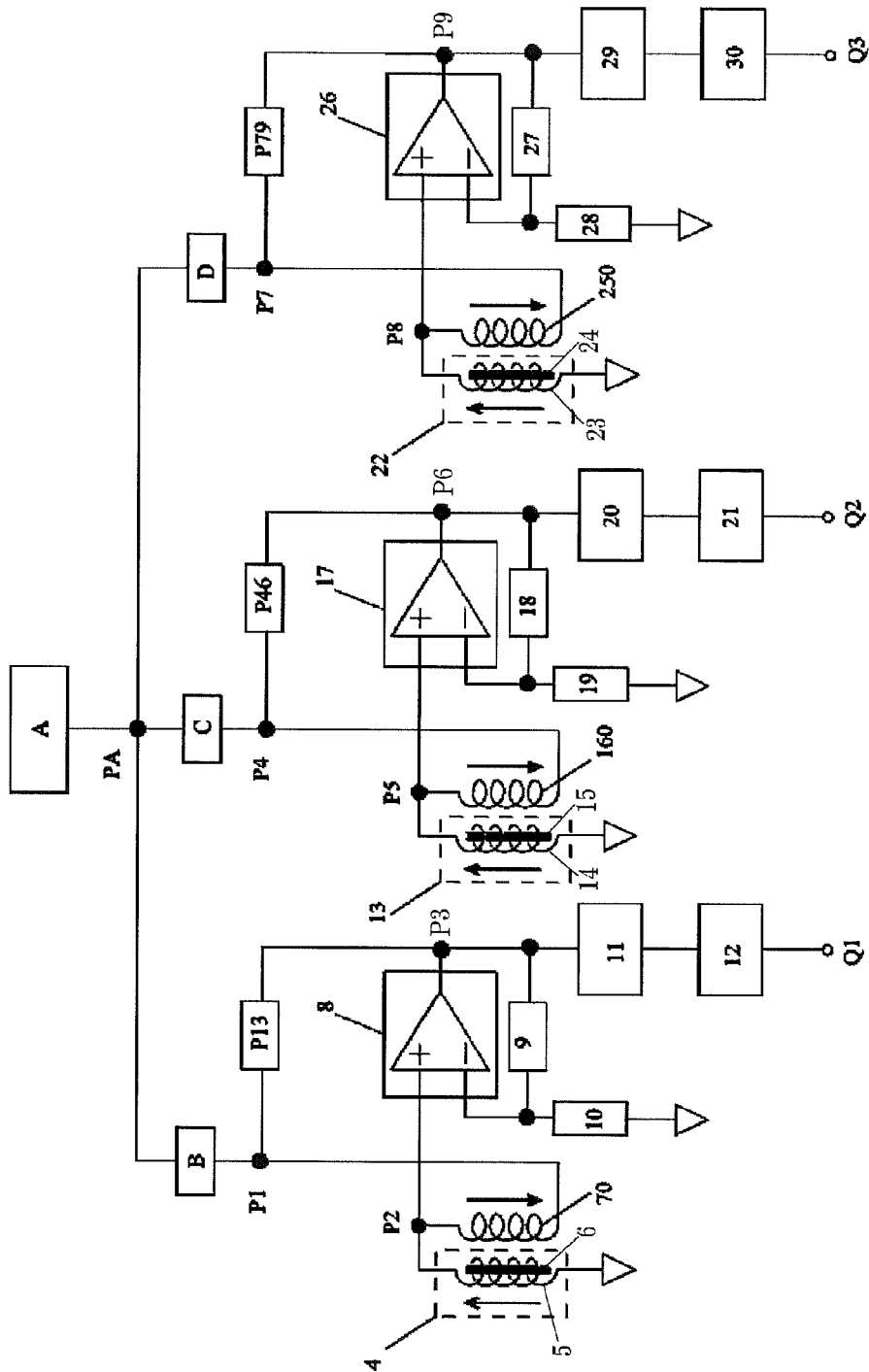
FIG. 6 is a circuit diagram of a magnetism detection device in accordance with the third embodiment of the present invention.
Figure 7:
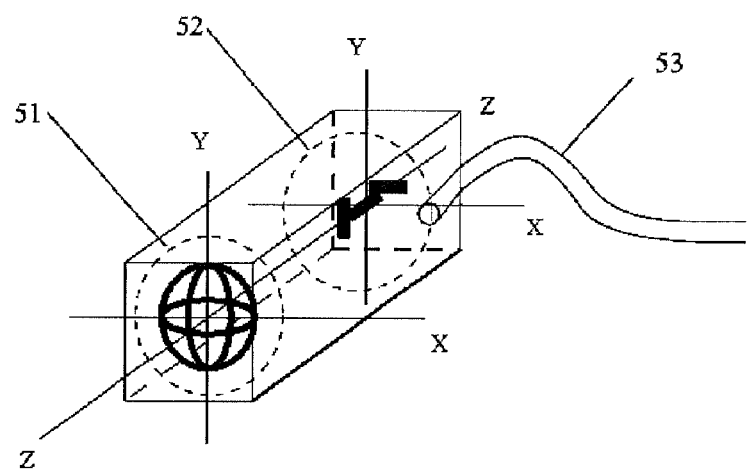
FIG. 7 is used for explaining the magnetic sensor disclosed in the patent document 1.

FIG. 6 illustrates a circuit in accordance with the third embodiment, in which a star-type oscillation synchronization signal circuit network is constructed for transmitting an oscillation synchronization signal, and a circuit for transmitting an external signal is added to the circuit network. A magnetic oscillation frequency is fixed by an oscillation synchronization signal output from the external signal transmitting circuit to thereby completely prevent occurrence of beat phenomenon caused by a difference among magnetic oscillation frequencies.

The star-type oscillation synchronization signal circuit network for transmitting an oscillation synchronization signal is comprised of a circuit in which one of terminals of a passive or active element electrically connected to operational amplifier circuits of a plurality of magnetic oscillation sensors is electrically connected to a common terminal PA through electrical connectors. If the circuit is viewed from the common terminal PA towards the magnetic oscillation sensors, wires are radially spread like star lights towards the magnetic oscillation sensors to define a star-shaped circuit network. Thus, this is called a star-type oscillation synchronization signal circuit network.

That is, an oscillation signal running through the oscillation synchronization signal circuit network is a signal having a fixed frequency, output from the external signal transmitting circuit. Since an excitation current commonly has the fixed frequency as an oscillation frequency, the cores of the magnetism sensing parts are excited with the unified magnetic oscillation frequency by virtue of a synthesized excitation current comprised of the oscillation synchronization current and an excitation current output from an operational amplifier circuit. The star-type oscillation synchronization signal circuit network is one of practically extremely useful oscillation synchronization signal circuit networks.

However, since a magnetic oscillation sensor is of an independent self-exciting system in which an excitation current is generated by a circuit of the sensor itself, it may be influenced by a magnetic field in dependence on a strength of a magnetic field to be measured. Specifically, there are generated fluctuation in an oscillation frequency and/or slight fluctuation in a unified magnetic oscillation frequency.

Since these phenomena act as a bar for measuring a magnetic field with high accuracy, it is necessary to prevent occurrence of slight fluctuation in a unified magnetic oscillation frequency. To this end, it is necessary to use an oscillation synchronization signal transmitted from an external oscillation circuit to thereby completely fix a magnetic oscillation frequency, as being carried out in the embodiment illustrated in FIG. 6.

An oscillation synchronization signal transmitted from an external oscillation circuit and having a unified magnetic oscillation frequency passes through the star-type oscillation synchronization signal circuit network constructed by the connection of electric connectors, joins an excitation current transmitted from the operational amplifier circuit, and magnetizes each of the cores of the magnetism sensing parts as a synthesized excitation current having a unified magnetic oscillation frequency.

That is, a fixed oscillation synchronization signal transmitted from the external signal transmitting circuit and running through the oscillation synchronization signal circuit network, and an excitation current compulsorily magnetize, with a unified magnetic oscillation frequency, each of the cores of the magnetism sensing parts.

In FIG. 6, the reference numeral A indicates a circuit for transmitting an external signal. The circuit is additionally connected to the common terminal PA outside of the star-type oscillation synchronization signal circuit network of the magnetic oscillation sensor circuit. The external signal transmitting circuit A is designed to have such a frequency that a magnetic oscillation sensor can be most stably oscillated therewith. An oscillation synchronization signal having the frequency is transmitted to each of the coils through the common terminal PA, the electric connectors B, C and D, and the terminals P1, P4 and P7.

Each of the cores 6, 15 and 24 in the core-coils 5, 14 and 23 of the magnetism sensing parts 4, 13 and 22 is excited by a synthesized excitation current comprised of a fixed oscillation synchronization signal transmitted from the external signal transmitting circuit and an excitation current transmitted from the operational amplifier circuit, the synthesized excitation current having a unified magnetic oscillation synchronization frequency which is stable and has no frequency fluctuation.

In other words, the embodiment illustrated in FIG. 6 further improves weak points of a star-type oscillation synchronization signal circuit network, and is an embodiment of a magnetism detecting device in which a frequency of an oscillation synchronization signal in the star-type oscillation synchronization signal circuit network is synchronized with and is fixed to a frequency of an electric signal transmitted from the external signal transmitting circuit, by electrically connecting the external signal transmitting circuit transmitting an electric signal having the same frequency as the unified magnetic oscillation synchronization frequency, and the operational amplifier circuit to each other through electric connectors.

Each of the connectors B, C and D is comprised of an electrically passive or active element, similarly to the connectors illustrated in FIG. 4.

In the case that each of P13, P46 and P79 is comprised of a resistance or a coil as a passive element, an impedance thereof is optimally determined such that magnetic oscillation stably continues even in the case that the circuit is short-circuited.

The technique relating to the external synchronization signal suppresses fluctuation in a magnetic oscillation frequency generated when a strong field is measured by means of a single magnetic oscillation sensor or even a plurality of magnetic oscillation sensors, and can be applied to a magnetic sensor used when an external magnetic field is uniaxially measured with high accuracy or measured simultaneously at a plurality of points. Thus, the technique is practically very useful.

One or more embodiments of the present invention can be used for measuring a leakage magnetic field existing in or out of a body of a train or an automobile, as technique for improving a magnetic oscillation sensor and a magnetism detecting device, so as to allow a magnetic sensor to accomplish best performances thereof.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

INDICATION BY REFERENCE NUMERALS 1, 2, 3 Connector
4, 13, 22 Magnetism sensing part
5, 14, 23 Core-coil
6, 15, 24 Core
7, 16, 25 Passive element
8, 17, 26 Operational amplifier circuit
9, 10, 18, 19, 27 28 Resistance
11, 20, 29 Filter circuit
12, 21, 30 Amplifying circuit
70, 160, 250 Air core coil
1000 X-axis circuit part
2000 Y-axis circuit part
3000 Z-axis circuit part

The invention claimed is:
1. An apparatus for detecting magnetism, comprising:
a self-exciting fluxgate type magnetic oscillation sensor in each of three axes perpendicular to one another, the magnetic oscillation sensor comprising:
  a magnetism sensor comprised of a core-coil including a core made of a magnetic material, and a coil wound around the core; and
  an operational amplifier circuit causing an AC excitation current to run through the coil to generate an output in accordance with a strength of an external magnetic field applied to the core,
wherein an air core coil not wound around a core is arranged in the vicinity of and in parallel with the core-coil of each of the magnetic oscillation sensors arranged in each of the axes,
wherein a node, through which a non-earthed terminal of the core-coil in each of the axes and one of terminals of the air core coil are electrically connected, to a non-inverted input terminal of the operational amplifier circuit, wherein the other terminal of the air core coil and an output terminal of the operational amplifier circuit are electrically connected to each other through a passive element, wherein when the core-coil of the magnetism sensor is excited with an excitation current, the operational amplifier circuit generates a current by which a magnetic field having the same strength as that of the leakage magnetic field and having a direction opposite to a direction of the leakage magnetic field is generated, and supplies the current to the air core coil, wherein an output terminal of the operational amplifier circuit included in the magnetic oscillation sensor in each of the axes and a terminal of the air core coil in the subsequent axis are electrically connected to each other through an electrical connector to construct a loop-type oscillation-synchronization signal circuit network for unifying oscillation frequencies of the magnetic oscillation sensors in each of the axes, in order to avoid beat phenomenon caused by a difference among oscillation frequencies of the magnetic oscillation sensors in the axes, and wherein a core of the magnetism sensor is compulsorily excited by a unified magnetic oscillation frequency by virtue of an excitation current comprised of a combination of an oscillation-synchronization signal running through the oscillation-synchronization signal circuit network, and an excitation current output from the operational amplifier circuit.

2. An apparatus for detecting magnetism, comprising:
a self-exciting fluxgate type magnetic oscillation sensor in each of three axes perpendicular to one another,
the magnetic oscillation sensor comprising:
   a magnetism sensor comprised of a core-coil including a core made of a magnetic material, and
   a coil wound around the core; and
   an operational amplifier circuit causing an AC excitation current to run through the coil to generate an output in accordance with a strength of an external magnetic field applied to the core,
wherein an air core coil not wound around a core is arranged in the vicinity of and in parallel with the core-coil of each of the magnetic oscillation sensors arranged in each of the axes, wherein a node, through which a non-earthed terminal of the core-coil in each of the axes and one of terminals of the air core coil are electrically connected, to a non-inverted input terminal of the operational amplifier circuit, wherein the other terminal of the air core coil and an output terminal of the operational amplifier circuit are electrically connected to each other through a passive element, wherein when the core-coil of the magnetism sensor is excited with an excitation current, the operational amplifier circuit generates a current by which a magnetic field having the same strength as that of the leakage magnetic field and having a direction opposite to a direction of the leakage magnetic field is generated, and supplies the current to the air core coil, wherein a terminal of the air core coil in each of the axes and a common terminal are electrically connected to each other through an electrical connector to construct a star-type oscillation-synchronization signal circuit network for unifying oscillation frequencies of the magnetic oscillation sensors in each of the axes, in order to avoid beat phenomenon caused by a difference among oscillation frequencies of the magnetic oscillation sensors in the axes, and wherein a core of the magnetism sensor is compulsorily excited by a unified magnetic oscillation frequency by virtue of an excitation current comprised of a combination of an oscillation-synchronization signal running through the oscillation-synchronization signal circuit network, and an excitation current output from the operational amplifier circuit.

3. The apparatus as set forth in claim 2, wherein an external signal transmitting circuit for transmitting an electric signal having the same frequency as that of the unified magnetic oscillation frequency and the common terminal are electrically connected to each other to construct an oscillation-synchronization signal circuit network in which a unified magnetic oscillation frequency is fixed.

* * * * *